United States Patent

Varma

[11] 4,397,782
[45] Aug. 9, 1983

[54] ANTIINFLAMMATORY 17-SPIROANDROSTENES

[75] Inventor: Ravi K. Varma, Belle Mead, N.J.

[73] Assignee: E. R. Squibb & Sons, Inc., Princeton, N.J.

[21] Appl. No.: 382,891

[22] Filed: May 28, 1982

[51] Int. Cl.³ .............................................. C07J 71/00
[52] U.S. Cl. .............................. 260/239.5; 260/239.55
[58] Field of Search ......................... 260/239.5, 239.55

[56]  References Cited
U.S. PATENT DOCUMENTS

| | | | |
|---|---|---|---|
| 3,338,929 | 8/1967 | Klimstra et al. | 260/397.45 |
| 3,757,009 | 9/1973 | Anner | 260/239.55 R |
| 4,091,036 | 5/1978 | Varma | 260/397.45 |
| 4,094,840 | 6/1978 | Varma | 260/239.55 R |
| 4,133,811 | 1/1979 | Varma | 260/239.55 R |
| 4,146,538 | 3/1979 | Varma et al. | 260/239.55 R |
| 4,243,586 | 1/1981 | Chao et al. | 260/239.55 R |

Primary Examiner—Elbert L. Roberts
Attorney, Agent, or Firm—Lawrence S. Levinson; Donald J. Barrack

[57] ABSTRACT

Topical antiinflammatory activity is exhibited by steroids having the formula

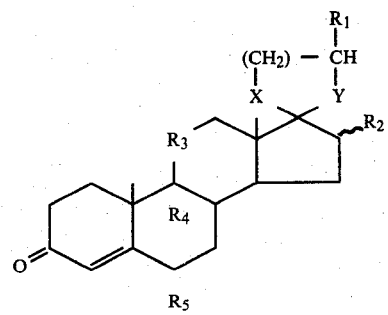

and the 1,2-dehydro and 15,16-dehydro derivatives thereof, wherein $R_1$ is hydrogen, alkyl, carboxyl, or alkoxycarbonyl;
$R_2$ is hydrogen, chlorine, bromine, fluorine, methyl, hydroxyl or a conventional hydrolyzable ester thereof, methoxy, or oxo (=O);
$R_3$ is carbonyl or $\beta$-hydroxymethylene;
$R_4$ is hydrogen or fluorine;
$R_5$ is hydrogen, methyl or fluorine;
X and Y are the same or different, and each is S, O, NH, N—CH$_3$, SO or SO$_2$; and
n is 1, 2, 3, 4 or 5.

22 Claims, No Drawings

ANTIINFLAMMATORY 17-SPIROANDROSTENES

BACKGROUND OF THE INVENTION

U.S. Pat. No. 4,243,586, issued Jan. 6, 1981 to Chao and Varma discloses various 17-spirodihydrofuranone androstenes having the partial structural formula

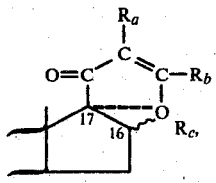

wherein $R_a$ is bromine, chlorine or fluorine; $R_b$ is alkyl, aryl or arylalkyl; and $R_c$ is hydrogen, α-methyl, β-methyl, hydroxy or a conventional hydrolyzable ester thereof. The steroids have antiinflammatory activity.

U.S. Pat. No. 3,757,009, issued Sept. 4, 1973 to Anner discloses various 17-spirodihydrofuranone androstenes having the partial structural formula

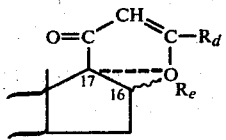

wherein $R_d$ is hydrogen, lower alkyl, or aralkyl and $R_e$ is hydrogen, methyl, free or esterified hydroxyl or β-halogen. The steroids have antiinflammatory activity.

U.S. Pat. Nos. 4,091,036, issued May 23, 1978, 4,094,840, issued June 13, 1978, 4,133,811, issued Jan. 9, 1979, and 4,146,538, issued Mar. 27, 1979, each discloses androstene intermediates having the partial structural formula

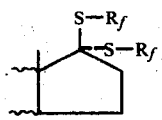

wherein $R_f$ is alkyl or aryl, and both $R_f$ groups are the same.

RELATED APPLICATION

U.S. patent application Ser. No. 294,680, filed Aug. 20, 1981 now U.S. Pat. No. 4,361,559, issued Nov. 30, 1982, discloses 17,17-bis-(substituted thio)androstenes having the partial structural formula

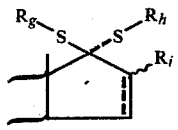

wherein $R_g$ and $R_h$ are the same or different and each is alkyl, cycloalkyl, or aryl; $R_i$ is hydrogen, hydroxy, alkoxy, aryloxy, alkylthio, arylthio, alkyl

or halogen; and the broken line in the 15,16-position represents the optional presence of ethylenic unsaturation. The steroids have antiinflammatory activity.

BRIEF DESCRIPTION OF THE INVENTION

Steroids having the formula

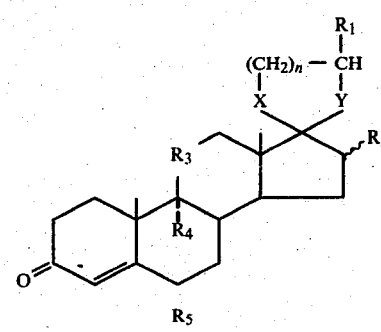

and the 1,2-dehydro and 15,16-dehydro derivatives thereof, have topical antiinflammatory activity. In formula I, and throughout the specification, the symbols are as defined below.

$R_1$ is hydrogen, alkyl, carboxyl, or alkoxycarbonyl;

$R_2$ is hydrogen, chlorine, bromine, fluorine, methyl, hydroxyl or a conventional hydrolyzable ester thereof, methoxy, or oxo ($=O$);

$R_3$ is carbonyl or β-hydroxymethylene;

$R_4$ is hydrogen or fluorine;

$R_5$ is hydrogen, methyl or fluorine;

X and Y are the same or different, and each is S, O, NH, N—CH₃, SO or SO₂; and n is 1,2,3,4 or 5.

The terms "alkyl" and "alkoxy" as used throughout the specification, either individually or as part of a larger group, refer to groups having 1 to 8 carbon atoms.

The term "aryl", as used throughout the specification, either individually or as part of a larger group, refers to phenyl or phenyl substituted with one or two alkyl, alkoxy, or halogen (chlorine, fluorine, bromine or iodine) groups.

The term "conventional hydrolyzable ester", as used throughout the specification, refers to those hydrolyzable carboxylic acid ester groups conventionally employed in the steroid art, particularly those derived from carboxylic acids having the formula

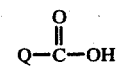

wherein Q is alkyl or aryl.

DETAILED DESCRIPTION OF THE INVENTION

The steroids of this invention can be prepared from starting steroids having the formula

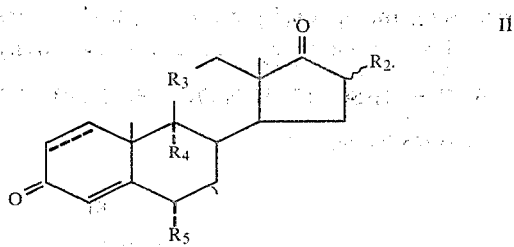

In formula II, and throughout the specification, the broken line in the 1,2-position represents the optional presence of ethylenic unsaturation.

Reaction of a steroid of formula II with a compound having the formula

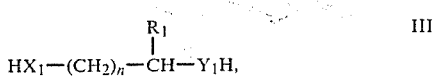

or a salt thereof, yields the corresponding product having the formula

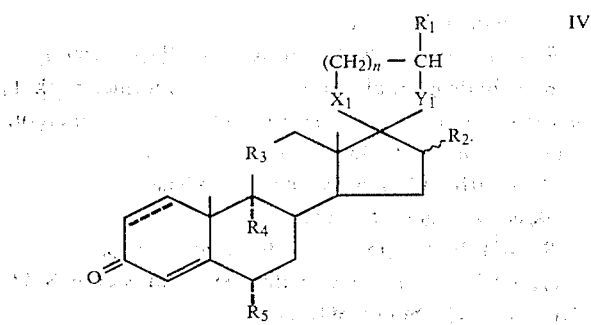

In formulas III and IV, and throughout the specification, the symbols $X_1$ and $Y_1$ are S, O, NH or N—CH$_3$. If $X_1$ and $Y_1$ are each sulfur, each oxygen, or one of $X_1$ and $Y_1$ is sulfur and the other is oxygen, the above reaction is preferably run in the presence of a Lewis acid (e.g., boron trifluoride etherate) in an organic solvent such as glacial acetic acid. If one of $X_1$ and $Y_1$ is imino or methylamino, the above reaction is preferably run in the presence of an organic base such as pyridine. If $R_2$ is hydrogen, the 17-oxo group of a steroid of formula II will be more reactive than the other oxo group(s) present and the desired product will be obtained. However, if $R_2$ is other than hydrogen, the 17-oxo group will be hindered and the compound of formula III will react with the other oxo groups in addition to the one in the 17-position. Cleavage of the substituents from the 3 and/or 11-positions can be accomplished using known techniques, such as treatment with methyl iodide/acetone/water.

Those products of formula I wherein X and/or Y are SO or SO$_2$ can be prepared by oxidation of the corresponding product wherein X and/or Y is sulfur. The use of the appropriate number of equivalents of an oxidizing agent such as m-chloroperoxybenzoic acid, yields the desired product.

Alternatively, the steroids of this invention wherein $R_2$ is hydrogen can be prepared from starting steroids having the formula

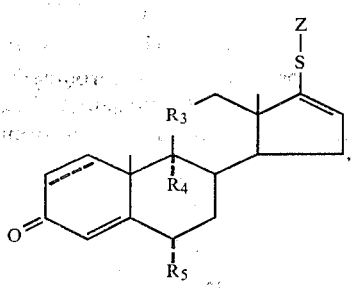

wherein Z is alkyl or aryl. Steroids of formula V can be prepared using the procedure described in U.S. Pat. No. 4,091,036.

Reaction of a steroid of formula V with mercuric chloride (to cleave the 17-substitent) and a compound of formula III yields the corresponding product of formula I wherein $R_2$ is hydrogen. The reaction can be run in an organic solvent under anhydrous conditions. Preferably, a drying agent such as 2-methyl-2-ethyl-1,3-dioxalane will also be present.

The steroids of formula I having ethylenic unsaturation in the 15,16-position can be prepared from the corresponding 16-haloandrostene. Refluxing the 16-haloandrostene in an organic solvent in the presence of 1,5-diazabicyclo (5.4.0) undec-5-ene yields the desired 15,16-unsaturation. Alternatively, the steroids of formula I having ethylenic unsaturation in the 15,16-position can be prepared from the correponding 16-hydroxyandrostene. Dehydrating the 16-hydroxyandrostene, using a dehydrating agent such as thionyl chloride, yields the desired 15,16-unsaturation.

The starting androstenes of formula II can be prepared by treating the corresponding pregnene having the formula

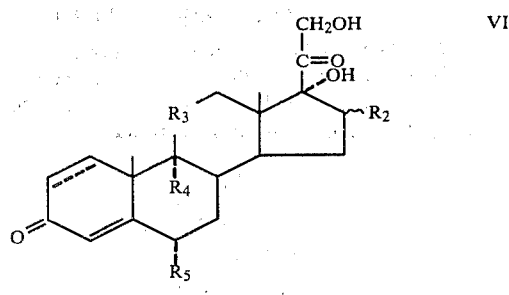

with sodium bismuthate in the presence of an acid such as acetic acid.

Alternatively, the starting androstenes of formula II wherein $R_2$ is hydroxy or a conventional hydrolyzable ester thereof, can be prepared by oxidation of the corresponding androstene having the formula

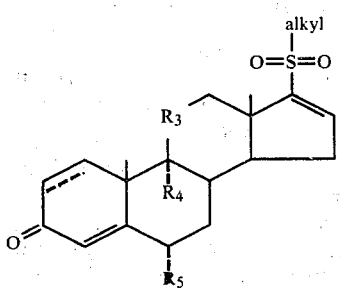

with potassium permanganate in the presence of formic acid. The oxidation reaction yields the corresponding 16α-hydroxyandrostene-3,17-dione. This can be acylated using art-recognized procedures to yield the corresponding 17-acyloxy derivative.

The steroids of formula I can be used to treat skin conditions such as dermatitis, psoriasis, sunburn, eczema, neurodermatitis, or anogenital pruritus, and in inhalation therapy for topical treatment of allergy and asthma.

For the treatment of skin conditions, the steroids of this invention may be administered in a conventional pharmaceutical carrier in the form of a cream, ointment, lotion or the like. The steroids will preferably be used in the range of 0.01 to 5.0% by weight of the vehicle, preferably 0.05 to 2.0% by weight of the vehicle.

For the topical treatment of allergy and asthma, the steroids of this invention may be administered in the conventional manner, e.g., as solid medicament which has been atomized. U.S. Pat. Nos. 3,948,264 and 4,147,166 are exemplary of the literature which describes devices that can be used to administer solid medicaments for inhalation therapy.

The following examples are specific embodiments of this invention.

EXAMPLE 1

(11β,16β)-9-Fluoro-11-hydroxy-16-methylandrosta-1,4-diene-3,17-dione,cyclic 17-(1,2-ethanediyl mercaptole)

(A)

9-Fluoro-11β-hydroxy-16β-methylandrosta-1,4-diene-3,17-dione

A solution of 4.7 g (12.0 mmole) of 9-fluoro-16β-methyl-11β,17,21-trihydroxypregna-1,4-diene-3,20-dione in 50% acetic acid (600 ml) was stirred with 18 g of sodium bismuthate at room temperature for 2 hours. The brown suspension was filtered through a bed of deactivated silica powder and washed with 100 ml of 50% acetic acid. The filtrate was concentrated in vacuo to 100 ml, diluted with 100 ml of 20% hydrochloric acid and extracted with chloroform. The chloroform solution was washed with 20% hydrochloric acid and water, dried over anhydrous Na₂SO₄ and evaporated in vacuo to give a solid. This was dissolved in chloroform and chromatographed on a 30 g silica gel column, eluting successively with chloroform and 1:4 ethyl acetate-chloroform to give 2.6 g of the title compound, melting point 281°-283° C., dec.

(B)

(11β,16β)-9-Fluoro-11-hydroxy-16-methylandrosta-1,4-diene-3,17-dione, cyclic 17-(1,2-ethanediyl mercaptole)

A solution of 1.0 g (3.01 mmole) of 9-fluoro-11β-hydroxy-16β-methylandrosta-1,4-diene-3,17-dione, 1.5 ml (1.79 mmole) of ethanedithiol and 1.0 ml (8.13 mmole) of boron trifluoride etherate in 50 ml of glacial acetic acid was stirred at room temperature under nitrogen overnight. The resulting solution was poured into cold water and extracted with chloroform. The chloroform solution was washed with water, saturated sodium bicarbonate solution and water, dried over anhydrous Na₂SO₄ and evaporated in vacuo to give a gummy material. This was mixed with acetone (125 ml), water (7 ml) and methyl iodide (7 ml) and refluxed for 7 hours. The resulting solution was evaporated in vacuo to give a slurry. This was diluted with chloroform, washed with 10% sodium thiosulfate solution and water, dried over anhydrous Na₂SO₄ and evaporated in vacuo to give a gummy material. This was dissolved in chloroform and chromatographed on 3 precoated silica gel TLC plates (Uniplate, 20 cm×20 cm×2 mm, 1:4 ethyl acetate-chloroform for development) to give in order of increasing polarity the following compounds: 300 mg of overreacted steroid; 110 mg of another steroid compound; 420 mg of the title compound and 100 mg of the starting steroid. The title compound (420 mg) was crystallized from acetone-hexane to give 340 mg of an analytical specimen, melting point 241°-242° C., dec.

Anal. Calc'd for $C_{22}H_{29}FO_2S_2$: C, 64.67; H, 7.15; F, 4.65; S, 15.70. Found: C, 64.51; H, 7.16; F, 4.71; S, 15.56.

EXAMPLE 2

(11β)-9-Fluoro-11-hydroxyandrosta-1,4-diene-3,17-dione,cyclic 17-(1,2-ethanediyl mercaptole)

A solution of 1.0 g (3.14 mmole) of 9-fluoro-11β-hydroxyandrosta-1,4-diene-3,17-dione, 1.0 ml of ethanedithiol, 10 ml of glacial acetic acid, 10 ml of dry dichloromethane and 0.25 ml of boron trifluoride etherate was stirred at room temperature under a nitrogen atmosphere for 2.5 hours. The solvent was evaporated in vacuo at room temperature. The residue was dissolved in chloroform, washed with saturated sodium bicarbonate and water, dried over anhydrous Na₂SO₄ and evaporated in vacuo to give a foam. This was redissolved in 1:4 hexane-chloroform and chromatographed on a 30 g silica gel column. Elutions successively with hexane-chloroform (1:4), chloroform and ethyl acetate-chloroform (5:95) gave 660 mg of the title compound. Crystallization from acetone-hexane gave 560 mg of an analytical specimen, melting point 277°-278° C., dec.

Anal. Calc'd for $C_{21}H_{27}FO_2S_2$: C, 63.92; H, 6.90; F, 4.82; S, 16.25. Found: C, 63.69; H, 6.88; F, 4.52; S, 16.16.

EXAMPLE 3

(11β,16β)-9-Fluoro-11-hydroxy-16-methylandrosta-1,4-diene-3,17-dione, cyclic 17-(1,3-propanediyl mercaptole)

A solution of 1.0 g (3.01 mmole) of 9-fluoro-11β-hydroxy-16β-methylandrosta-1,4-diene-3,17-dione (see example 1A), 2 ml of 1,3-propanedithiol and 1.5 ml of boron trifluoride etherate in 50 ml of glacial acetic acid was stirred at room temperature under nitrogen overnight. The resulting solution was poured into cold water and extracted with chloroform. The chloroform solution was washed with saturated sodium bicarbonate and water, dried over anhydrous Na$_2$SO$_4$, and evaporated in vacuo to give a gummy material. This was mixed with acetone (125 ml), water (5 ml) and methyl iodide (7 ml) and refluxed for 5 hours. The resulting solution was evaporated in vacuo to give a slurry. This was diluted with chloroform, washed with 10% sodium thiosulfate solution and water, dried over anhydrous Na$_2$SO$_4$ and evaporated in vacuo to give a gummy material. This was dissolved in chloroform and chromatographed on 3 precoated silica gel TLC plates (Uniplate, 20 cm×20 cm×2 mm, 1:4 ethyl acetate-chloroform for development) to give in order of increasing polarity the following compounds: 150 mg of over-reacted steroid, 125 mg of a steroidal side-product, 300 mg of the title compound and 250 mg of the starting steroid. Crystallization from acetone-hexane gave 225 mg of an analytical specimen, melting point 217°–219° C., dec.

Anal. Calc'd for C$_{23}$H$_{31}$FO$_2$S$_2$: C, 65.36; H, 7.39; F, 4.50; S, 15.17. Found: C, 65.14; H, 7.55; F, 4.46; S, 15.13.

EXAMPLE 4

(11β)-9-Fluoro-11-hydroxyandrosta-1,4-diene-3,17-dione, cyclic 17-(1,3-propanediyl mercaptole)

A solution of 1.0 g (3.14 mmole) of 9-fluoro-11β-hydroxyandrosta-1,4-diene-3,17-dione, 1.0 ml of 1,3-propanedithiol, 10 ml of glacial acetic acid, 10 ml of dry dichloromethane and 0.25 ml of boron trifluoride etherate was stirred at room temperature under a nitrogen atmosphere for 2.5 hours. The resulting solution was diluted with chloroform, washed with saturated sodium bicarbonate and water, dried over anhydrous Na$_2$SO$_4$ and evaporated in vacuo to give a foam. This was redissolved in 1:9 hexane-chloroform and chromatographed on a 30 g silica gel column. Elutions successively with hexane-chloroform (1:9), chloroform and ethyl acetate-chloroform (5:95) gave 400 mg of the title compound. Crystallization from acetone-hexane gave 350 mg of an analytical specimen, melting point 193°–197° C., dec.

Anal. Calc'd for C$_{22}$H$_{29}$FO$_2$S$_2$: C, 64.67; H, 7.15; F, 4.65; S, 15.70. Found: C, 64.43; H, 7.43; F, 4.36; S, 15.74.

EXAMPLE 5

(11β,16α)-9-Fluoro-11-hydroxy-16-methylandrosta-1,4-diene-3,17-dione, cyclic 17-(1-3-propanediyl mercaptole)

(A)

9-Fluoro-11β-hydroxy-16α-methylandrosta-1,4-diene-3,17-dione

A solution of 33 g (84.09 mmole) of 9-fluoro-16α-methyl-11β,17,21-trihydroxypregna-1,4-diene-3,20-dione in 50% acetic acid (3 liters) was stirred with 320 g of sodium bismuthate at room temperature for 20 hours. The resulting brown suspension was filtered through a bed of deactivated silica powder and washed with 300 ml of 50% acetic acid. The filtrate was concentrated in vacuo to 500 ml, diluted with 250 ml of 20% hydrochloric acid and extracted with chloroform. The chloroform solution was washed with 20% hydrochloric acid and water, dried over anhydrous Na$_2$SO$_4$ and evaporated in vacuo to give a solid. This was dissolved in chloroform and chromatographed on a 250 g-silica gel column, eluting successively with chloroform and 1:4 ethyl acetate-chloroform to give 22.8 g (81.6%) of tlc-homogeneous title compound, melting point 240°–242° with consistent spectral data.

(B)

(11β,16α)-9-Fluoro-11-hydroxy-16-methylandrosta-1,4-diene-3,17-dione, cyclic 17-(1,3-propanediyl mercaptole)

A solution of 1.0 g (3.01 mmole) of 9-fluoro-11β-hydroxy-16α-methyl-androsta-1,4-diene-3,17-dione, 1.0 ml (9.97 mmole) of 1,3-propanedithiol, 0.8 ml (6.5 mmole) of boron trifluoride etherate and 0.32 ml (2.4 mmole) of N,N-dimethylformamide dimethyl acetal in 15 ml of glacial acetic acid was stirred at room temperature under nitrogen overnight. The resulting solution was poured into cold water and extracted with chloroform. The chloroform solution was washed with water, saturated sodium bicarbonate solution and water, dried over anhydrous Na$_2$SO$_4$ and evaporated in vacuo to give a foam. This was mixed with acetone (50 ml), water (1.0 ml) and methyl iodide (2 ml) and refluxed for 3.5 hours. The resulting solution was evaporated in vacuo to give a slurry. This was diluted with chloroform, washed with 10% sodium thiosulfate solution and water, dried over Na$_2$SO$_4$ and evaporated in vacuo to give a gummy material. This was dissolved in chloroform and chromatographed on 3 precoated silica gel TLC plates (Uniplate, 20 cm×20 cm×2 mm, 1:4 ethyl acetate-chloroform for development) to give in order of increasing polarity the following compounds: 105 mg of over-reacted steroid, 265 mg of the title compound and 420 mg of the starting steroid. The title compound (265 mg) was crystallized from acetone-hexane to give 215 mg of an analytical specimen, melting point 260°–261° C., dec.

Anal. Calc'd from C$_{23}$H$_{31}$FO$_2$S$_2$: C, 65.36; H, 7.39; F, 4.50; S, 15.17. Found: C, 65.06; H, 7.26; F, 4.51; S, 15.26.

EXAMPLE 6

(11β,16α)-9-Fluoro-11-hydroxy-16-methylandrosta-1,4-diene-3,17-dione, cyclic 17-(1,2-ethanediyl mercaptole)

A solution of 1.0 g (3.01 mmole) of 9-fluoro-11β-hydroxy-16α-methylandrosta-1,4-diene-3,17-dione (see example 5A), 1.0 ml (11.92 mmole) of 1,2-ethanedithiol and 0.8 ml (6.5 mmole) of boron trifluoride etherate in 10 ml of glacial acetic acid was stirred at room temperature under nitrogen for 7.0 hours. The resulting solution was diluted with chloroform, washed with water, saturated sodium bicarbonate and water, dried over anhydrous Na$_2$SO$_4$ and evaporated in vacuo to give a foam. This was mixed with acetone (50 ml), water (1.0 ml) and methyl iodide (2 ml) and refluxed for 6.5 hours. The resulting solution was evaporated in vacuo at room temperature to give a slurry. This was diluted with chloroform, washed with 10% sodium thiosulfate solution and water, dried over anhydrous Na$_2$SO$_4$ and evaporated in vacuo. The residue was dissolved in chloroform and chromatographed on 3 precoated silica gel TLC plates (Uniplates, 20 cm×20 cm×2 mm, 1:4 ethyl acetate-chloroform for development) to give in order of increasing polarity the following compounds: 105 mg of over-reacted steroid, 450 mg of the title compound and 360 mg of the starting steroid. The title compound (450 mg) was crystallized from acetone-hexane to give 350 mg of an analytical specimen, melting point 286°–287° C., dec.

Anal. Calc'd for C$_{22}$H$_{29}$FO$_2$S$_2$: C, 64.47; H, 7.15; F, 4.65; S, 15.70. Found: C, 64.42; H, 7.00; F, 4.63; S, 15.42.

EXAMPLE 7

(11β,17S)-9-Fluoro-11-hydroxyandrosta-1,4-diene-3,17-dione, cyclic 17-[(oxyethylene)thio]mixed acetal A solution of 1.0 g (3.14 mmole) of 9-fluoro-11β-hydroxyandrosta-1,4-diene-3,17-dione, 2.0 ml of 2-mercaptoethanol, 10 ml of glacial acetic acid, 10 ml of dry dichloromethane and 0.5 ml of boron trifluoride etherate was stirred at room temperature under nitrogen for 1.0 hour. The resulting solution was diluted with dichloromethane, washed with saturated sodium bicarbonate solution and water, dried over anhydrous Na$_2$SO$_4$ and was evaporated in vacuo to give a gum. This was combined with the product from another run (using 0.5 g of steroid as starting material), dissolved in chloroform and chromatographed on a 40 g silica gel column, eluting successively with chloroform, ethyl acetate-chloroform (5:95 and 10:90) and methanol-chloroform (1:9), to give 1.0 g of slightly impure title compound and 375 mg of starting steroid. The impure title compound (1.0 g) was crystallized from acetone-hexane to give 500 mg of an analytical specimen, melting point 254°–260° C., dec.

Anal. Calc'd for C$_{21}$H$_{27}$FO$_3$S: C, 66.63; H, 7.19; F, 5.02; S, 8.47. Found: C, 66.76; H, 7.18; F, 4.83; S, 8.37.

EXAMPLE 8

(11β,17S)-9-Fluoro-11-hydroxyspiro[androsta-1,4-diene-17,2'-[1,3]-oxathiolane]-3-one, 3',3'-dioxide

(A)

(11β,17S)-9-Fluoro-11-hydroxyspiro[androsta-1,4-diene-17,2'-[1,3]-oxathiolane]-3-one,3'-oxide To a solution of 1.0 g (2.64 mmole) of (11β,17S)-9-fluoro-11-hydroxy-androsta-1,4-diene,-3,17-dione, cyclic 17-[(oxoethylene)thio] mixed acetal (see example 7) in 200 ml of dichloromethane was added a solution of 600 mg of m-chloroperoxybenzoic acid in 20 ml of dichloromethane in the course of 3 minutes. After the addition, the solution was stirred at room temperature for 30 minutes, washed with a saturated sodium bicarbonate solution and water, dried over anhydrous Na$_2$SO$_4$ and was evaporated in vacuo to give 1.0 g of the title compound (a mixture of two sulfoxide isomers), separable by tlc; melting point 234°–245° C., dec.

(B)

(11β,17S)-9-Fluoro-11-hydroxyspiro[androsta-1,4-diene-17,2'-[1,3]-oxathiolane]-3-one,3',3-dioxide A solution of 1.0 g (2.53 mmole) of (11β,17S)-9-fluoro-11-hydroxyspiro[androsta-1,4-diene-17,2'-[1,3]-oxathiolane]-3-one,3'-oxide (a mixture of two sulfoxide isomers) in 450 ml of dichloromethane and 15 ml of methanol was stirred with 546 mg of 85% m-chloroperoxybenzoic acid at room temperature for 30 minutes. On the basis of tlc (silica gel; 1:9 methanol-chloroform development) only one of two sulfoxide isomers (the more polar isomer) reacted completely to give the sulfone (the title compound). The solution was stirred at room temperature overnight, but this did not have any significant effect on the course of the reaction as discerned by tlc. The resulting solution was washed with a saturated sodium bicarbonate solution and water, dried over anhydrous Na$_2$SO$_4$ and evaporated in vacuo to give a solid. This was dissolved in chloroform-methanol (1:1) and chromatographed on 4 precoated silica gel TLC plates (E. Merck, 20 cm×20 cm×2 mm, 1:9 methanol-chloroform for development) to give 560 mg of the title compound and 330 mg of unreacted sulfoxide (the less polar isomer). The titled compound (560 mg) was recrystallized from chloroform-methanol to give 450 mg (43.2%) of an analytical specimen, melting point 223°–225° C., dec.

Anal. Calc'd for C$_{21}$H$_{27}$FO$_5$S: C, 61.44; H, 6.63 F, 4.63; S, 7.81. Found: C, 61.22; H, 6.74; F, 4.62; S, 7.78.

EXAMPLE 9

(11β,17S)-9-Fluoro-11-hydroxyspiro[androsta-1,4-diene-17,2'[1,3]-oxathiolane]-3-one,3'-oxide (Isomer A)

The unreacted sulfoxide (the less polar (tlc) isomer, 330 mg; see example 8B) was recrystallized from methanol-chloroform to give 270 mg of an analytical specimen, melting point 244°–247° C., dec. On the basis of its relative inertness to m-chloroperoxybenzoic acid, and lower tlc polarity, this sulfoixde isomer has been assigned the S-configuration. The starting sulfoxide isomer mixture was isomerized cleanly into the title compound with 1,5-diazabicyclo(5.4.0)undec-5-ene.

Anal. Calc'd for C$_{21}$H$_{27}$FO$_4$S: C, 63.93; H, 6.90; F, 4.82; S, 8.13. Found: C, 63.62; H, 6.80; F, 4.91; S, 8.17.

EXAMPLE 10

(11β,17S)-9-Fluoro-11-hydroxyspiro[androsta-1,4-diene-17,2'[1,3]oxathiolane]-3-one,3'-oxide (Isomer B)

To a solution of 4.1 g (10.83 mmole) of (11β,17S)-9-fluoro-11-hydroxyandrosta-1,4-diene-3,17-dione, cyclic 17-[(oxyethylene)thio]mixed acetal (see example 7) in 700 ml of dichloromethane was added a solution of 2.42 g (12.0 mmole) of m-chloroperoxybenzoic acid (85.6%) in 100 ml of dichloromethane in the course of 10 minutes. The resulting solution was stirred at room temperature for 30 minutes, washed with a saturated sodium bicarbonate solution and water, dried over anhydrous Na$_2$SO$_4$ and evaporated in vacuo to give a foam (a mixture of two sulfoxide isomers in nearly equal amounts by tlc). This was rinsed with acetone and filtered. The solid (3.5 g) was a mixture of two sulfoxide isomers. The filtrate was concentrated in vacuo to give a foam which was enriched in the title compound (isomer B, the more polar isomer). Crystallization from methanol-chloroform gave 610 mg of an analytical specimen, melting point 189°–191° C., with consistent spectral data.

Anal. Calc'd for C$_{21}$H$_{27}$FO$_4$S: C, 63.93; H, 6.90; F, 4.82; S, 8.13. Found: C, 63.75; H, 6.79; F, 4.80; S, 8.04.

EXAMPLE 11

(11β,17R)-9-Fluoro-11-hydroxyandrosta-1,4-diene-3,17-dione, cyclic 17-[(oxyethylene)thio]mixed acetal A solution of 8.0 g (25.13 mmole) of 9-fluoro-11β-hydroxyandrosta-1,4-diene-3,17-dione, 16 ml of 2-mercaptoethanol, 80 ml of glacial acetic acid, 80 ml of dry dichloromethane and 5 ml of boron trifluoride etherate was stirred at room temperature under nitrogen for 1.0 hour. The resulting solution was diluted with chloroform, washed with water, a saturated sodium bicarbonate solution and water, dried over anhydrous Na$_2$SO$_4$ and evaporated in vacuo to give a solid. This was dissolved in chloroform and chromatographed on a 150 g silica gel column, eluting successively with chloroform and 1:9 ethyl acetate-chloroform to give 6.0 g of a mixture of (11β,17S)-9-fluoro-11-hydroxyandrosta-1,4-diene-3,17-dione, cyclic 17-[(oxyethylene)thio]mixed acetal and the title compound. Crystallization from ethyl acetate-hexane gave 4.0 g of (11β,17S)-9-fluoro-11-hydroxyandrosta-1,4-diene-3,17-dione, cyclic 17-[(oxyethylene)thio]mixed acetal. The mother liquor was rechromatographed on four precoated silica gel TLC plates (E. Merck, 20 cm×20 cm×2 mm, 1:4 ethyl acetate-chloroform development) to give 0.6 g more of (11β,17S)-9-fluoro-11-hydroxyandrosta-1,4-diene-3,17-dione, cyclic 17-[(oxyethylene)thio]mixed acetal and 520 mg of impure title compound. This (520 mg) was rinsed with ethyl acetate-hexane to give 240 mg of clean title compound. Another run using 7.0 g of starting steroid gave similarly 170 mg of title compound. These were combined and recrystallized from acetone-hexane to give 350 mg of an analytical specimen, melting point 260°-262° C.

Anal. Calc'd for $C_{21}H_{27}FO_3S$: C, 66.63; H, 7.19; F, 5.02; S, 8.47. Found: C, 66.43; H, 7.14; F, 4.91; S, 8.45.

EXAMPLE 12

(11β)-9-Fluoro-11-hydroxyspiro(pregna-1,4-diene-17,2'-thiazolidin)-3-one

A solution of 9-fluoro-11β-hydroxyandrosta-1,4-diene-3,17-dione (2.64 g; 8.3 mmole) in dry pyridine (60 ml) was mixed with 2-aminoethanethiol hydrochloride (1.09 g, 9.6 mmole) and was heated in a bath at 100° C. for about 5.0 hours. Another portion of the reagent (1.09 g, 9.6 mmole) was then added and the reaction was continued for another 3.0 hours. The mixture was then evaporated in vacuo to remove the pyridine. The residue was dissolved in dichloromethane and was washed successively with a 10% $Na_2CO_3$ solution and water, dried ($MgSO_4$ anhydrous) and was evaporated to afford an amorphous solid. This was chromatographed on a column of silica gel (35 g) eluting the column successively with dichloromethane, dichloromethane ethyl acetate (9:1 and 4:1) and dichloromethane-methanol (95:5 and 9:1), with tlc monitoring of the fractions, to isolate the title compound (565 mg). This material had a small amount of the starting ketone as impurity (tlc). One recrystallization from ethylacetate-hexane followed by drying (110° C., 0.3 mm; 8 hours) gave the analytical specimen (280 mg), melting point 227°-228° C.

Anal. Calc'd for $C_{21}H_{28}FNO_2S$: C, 66.81; H, 7.47 F, 5.03; N, 3.71; S, 8.49. Found: C, 66.97; H, 7.35; F, 4.99; N, 3.51; S, 8.29.

EXAMPLE 13

(11β)-9-Fluoro-11-hydroxyandrosta-1,4-diene-3,17-dione, cyclic 17-(1,2-ethanediyl acetal)

A solution of mercuric chloride (1.09 g), 2-methyl-2-ethyl-1,3-dioxolane (7.5 ml), dry ethylene glycol (7.5 ml), dry acetonitrile (45 ml) and dry dichloromethane (45 ml) was stirred at room temperature under nitrogen for one hour. To this solution was added 9-fluoro-11β-hydroxy-17β-(phenylthio)androsta-1,4,16-triene-3-one (1.5 g, 3.65 mmole) followed by dry dichloromethane (40 ml) to make a homogeneous solution. Generally, a solid started to separate from the solution. After overnight stirring the suspension was filtered and washed with dichloromethane. The filtrate and washings were combined, washed with saturated $NaHCO_3$ solution and water, dried over anhydrous $Na_2SO_4$ and evaporated in vacuo to give a solid. This was dissolved in chloroform and chromatographed on 45 g aluminum oxide (Welm, basic activity II) column. Elutions successively with chloroform, mixtures of ethyl acetate-chloroform (1:9, 1:4 and 3:7) and chloroform-methanol (9:1) gave 900 mg (68% of the tlc-homogeneous title compound). Crystallization from acetone-hexane gave 800 mg of an analytical specimen, melting point 303°-304° C., dec.

Anal. Calc'd for $C_{21}H_{27}FO_4$: C, 69.59; H, 7.51; F, 5.24. Found: C, 69.42; H, 7.36; F, 5.36.

What is claimed is:

1. A steroid having the formula

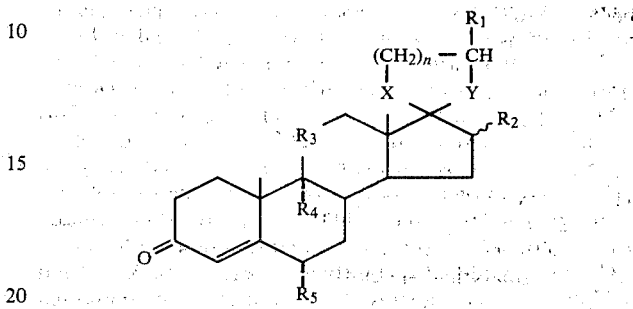

or the 1,2-dehydro and 15,16-dehydro derivatives thereof, wherein $R_1$ is hydrogen, alkyl, carboxyl, or alkoxycarbonyl;

$R_2$ is hydrogen, chlorine, bromine, fluorine, methyl, hydroxyl or a conventional hydrolyzable ester thereof, methoxy, or oxo;

$R_3$ is carbonyl or β-hydroxymethylene;

$R_4$ is hydrogen or fluorine;

$R_5$ is hydrogen, methyl or fluorine;

X and Y are the same or different, and each is S, O, NH, N—$CH_3$, SO or $SO_2$; and n is 1, 2, 3, 4 or 5; with the proviso that X and Y are not both O.

2. A steroid in accordance with claim 1 wherein $R_1$ is hydrogen, $R_3$ is β-hydroxymethylene, $R_4$ is fluorine and $R_5$ is hydrogen.

3. A steroid in accordance with claim 1 wherein both X and Y are S.

4. A steroid in accordance with claim 1 wherein one of X and Y is S and the other is O.

5. A steroid in accordance with claim 1 wherein one of X and Y is SO and the other is O.

6. A steroid in accordance with claim 1 wherein one of X and Y is $SO_2$ and the other is O.

7. A steroid in accordance with claim 1 wherein one of X and Y is S and the other is NH.

8. A steroid in accordance with claim 1 wherein n is 1 or 2.

9. The steroid in accordance with claim 1 (11β,16β)-9-fluoro-11-hydroxy-16-methylandrosta-1,4-diene-3,17-dione, cyclic 17-(1,2-ethanediyl mercaptole).

10. The steroid in accordance with claim 1 (11β)-9-fluoro-11-hydroxyandrosta-1,4-diene-3,17-dione, cyclic 17-(1,2-ethanediyl mercaptole).

11. The steroid in accordance with claim 1 (11β,16β)-9-fluoro-11-hydroxy-16-methylandrosta-1,4-diene-3,17-dione, cyclic 17-(1,3-propanediyl mercaptole).

12. The steroid in accordance with claim 1 (11β)-9-fluoro-11-hydroxyandrosta-1,4-diene-3,17-dione, cyclic 17-(1,3-propanediyl mercaptole).

13. The steroid in accordance with claim 1 (11β,16α)-9-fluoro-11-hydroxy-16-methylandrosta-1,4-diene-3,17-dione, cyclic 17-(1-3-propanediyl mercaptole).

14. The steroid in accordance with claim 1 (11β,16α)-9-fluoro-11-hydroxy-16-methylandrosta-1,4-diene-3,17-dione, cyclic 17-(1,2-ethanediyl mecaptole).

15. The steroid in accordance with claim 1 (11β,17S)-9-fluoro-11-hydroxyandrosta-1,4-diene-3,17-dione, cyclic 17-[(oxyethylene)thio]mixed acetal.

16. The steroid in accordance with claim 1 (11β,17S)-9-fluoro-11-hydroxyspiro[androsta-1,4-diene-17,2′-[1,3]-oxathiolane]-3-one, 3′,3′-dioxide.

17. The steroid in accordance with claim 1 (11β,17S)-9-fluoro-11-hydroxyspiro[androsta-1,4-diene-17,2′[1,3]-oxathiolane]-3-one,3′oxide (Isomer A).

18. The steroid in accordance with claim 1 (11β,17S)-9-fluoro-11-hydroxyspiro[androsta-1,4-diene-17,2′[1,3]oxathiolane]-3-one,3′-oxide (Isomer B).

19. The steroid in accordance with claim 1 (11β,17R)-9-fluoro-11-hydroxyandrosta-1,4-diene-3,17-dione, cyclic 17-[(oxyethylene)thio]mixed acetal.

20. The steroid in accordance with claim 1 (11β)-9-fluoro-11-hydroxyspiro(pregna-1,4-diene-17,2′-thiazolidin)-3-one.

21. A steroid having the formula

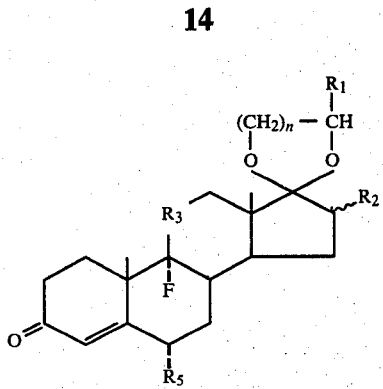

or the 1,2-dehydro and 15,16-dehydro derivatives thereof, wherein $R_1$ is hydrogen, alkyl, carboxyl, or alkoxycarbonyl;

$R_2$ is hydrogen, chlorine, bromine, fluorine, methyl, hydroxyl or a conventional hydrolyzable ester thereof, methoxy, or oxo;

$R_3$ is carbonyl or β-hydroxymethylene;

$R_5$ is hydrogen, methyl or fluorine;

n is 1, 2, 3, 4 or 5.

22. The steroid in accordance with claim 21 (11β)-9-fluoro-11-hydroxyandrosta-1,4-diene-3,17-dione, cyclic 17-(1,2-ethanediyl acetal).

* * * * *